(12) United States Patent
Dee et al.

(10) Patent No.: US 8,282,891 B2
(45) Date of Patent: Oct. 9, 2012

(54) APPARATUS FOR THE GENERATION OF GASES

(75) Inventors: Thomas J. Dee, Holliston, MA (US); Paul Sabin, Needham, MA (US); Douglas Sabin, Marblehead, MA (US)

(73) Assignee: TBS Technologies, LLC, Holliston, MA (US)

( * ) Notice: Subject to any disclaimer, the term of this patent is extended or adjusted under 35 U.S.C. 154(b) by 0 days.

(21) Appl. No.: 12/828,529

(22) Filed: Jul. 1, 2010

(65) Prior Publication Data

US 2011/0129390 A1 Jun. 2, 2011

Related U.S. Application Data

(63) Continuation of application No. 11/804,817, filed on May 21, 2007, now abandoned.

(51) Int. Cl.
| | |
|---|---|
| *B01J 7/02* | (2006.01) |
| *A61L 2/00* | (2006.01) |
| *A61L 2/18* | (2006.01) |
| *A61L 9/00* | (2006.01) |
| *B01J 19/00* | (2006.01) |
| *B01J 8/00* | (2006.01) |
| *B01J 7/00* | (2006.01) |
| *B01J 8/04* | (2006.01) |
| *G05D 16/00* | (2006.01) |
| *C01B 11/02* | (2006.01) |

(52) U.S. Cl. ............. 422/236; 422/28; 422/29; 422/292; 422/129; 422/130; 422/187; 422/305; 422/112; 422/113; 422/108; 422/600; 422/630; 422/644; 422/647; 422/648; 423/477; 423/478; 423/479; 423/480

(58) Field of Classification Search .......... 422/108–113, 422/129, 130, 187, 198, 224, 236, 305, 600, 422/630, 644, 647, 648, 28, 29, 292; 423/477–480
See application file for complete search history.

(56) References Cited

U.S. PATENT DOCUMENTS

| | | | | |
|---|---|---|---|---|
| 4,251,224 | A | * | 2/1981 | Cowley et al. ................ 423/477 |
| 4,886,653 | A | * | 12/1989 | Gasper et al. ................. 423/478 |
| 5,009,875 | A | * | 4/1991 | Kelley et al. .................. 423/477 |
| 5,258,171 | A | * | 11/1993 | Eltomi .......................... 423/477 |
| 5,651,996 | A | * | 7/1997 | Roozdar ....................... 424/665 |
| 6,238,643 | B1 | * | 5/2001 | Thangaraj et al. ............ 423/477 |

(Continued)

FOREIGN PATENT DOCUMENTS

EP 230737 A1 * 8/1987

(Continued)

OTHER PUBLICATIONS

Machine translation of the description of WO 03/078312 A1, which was published on Sep. 25, 2003.*
Machine translation of the claims of WO 03/078312 A1, which was published on Sep. 25, 2003.*

*Primary Examiner* — Walter D Griffin
*Assistant Examiner* — Natasha Young
(74) *Attorney, Agent, or Firm* — McCarter & English, LLP

(57) ABSTRACT

The instant application provides apparatus and methods for the generation of gas, preferably chlorine dioxide. The methods and apparatus of the invention use a removable reaction chamber for the reaction of precursor chemicals, e.g., chlorite salt and an acid. The methods and compositions of the invention provide gas for a number of personal and commercial applications.

78 Claims, 6 Drawing Sheets

U.S. PATENT DOCUMENTS

| | | | |
|---|---|---|---|
| 6,440,314 B1 * | 8/2002 | Simpson | 210/757 |
| 7,534,398 B2 * | 5/2009 | Dee et al. | 422/122 |
| 2004/0069719 A1 * | 4/2004 | Wang | 210/749 |
| 2004/0101438 A1 * | 5/2004 | Nelson et al. | 422/31 |
| 2004/0241065 A1 * | 12/2004 | Kampa et al. | 422/305 |
| 2005/0079124 A1 * | 4/2005 | Sanderson | 423/477 |
| 2006/0039841 A1 * | 2/2006 | Rico et al. | 422/305 |

FOREIGN PATENT DOCUMENTS

| | | | |
|---|---|---|---|
| WO | WO 03/078312 A1 * | 9/2003 | |
| WO | WO 2006/0068743 A2 * | 6/2006 | |

* cited by examiner

APPARATUS FOR THE GENERATION OF GASES

RELATED APPLICATION

This application is a continuation of U.S. application Ser. No. 11/804,817, filed May 21, 2007, now abandoned, the entire contents of which are hereby incorporated herein by reference.

FIELD OF THE INVENTION

The present invention relates to methods and apparatuses for the generation of gases using a disposable reaction chamber with the preferred embodiment being the generation of gaseous chlorine dioxide for small scale applications.

BACKGROUND OF THE INVENTION

Chlorine dioxide was discovered in the early 1800's, and was adopted by commerce in the United States in the 1940's. Chlorine dioxide has been called the ideal biocide and the ability of chlorine dioxide to reduce or eliminate microbes, e.g., bacteria, viruses, fungi, mold spores, algae and protozoa, is well-documented and well known. See, for example, Franklin, C. L. et al. (1991) *Am Vet Med Assoc* 198:1625-30; Korich K. G., et al. (1990) *Appl Environ Microbiol.* 56:1423-8; Boddie et al. (2000) *J Dairy Sci.* 83:2975-9; Lee et al. (2004) *J Food Prot.* 67:1371-6; Han et al. (2003) *J Environ Health* 66:16-21; Sy et al. (2005) *J Food Prot.* 68:1176-87; and LeChevallier M. W. et al. (1988) *Appl Environ Microbiol.* 54:2492-9.

Chlorine dioxide inactivates microorganisms by oxidizing key components of a microorganism's membrane proteins that are vital to the membrane's structure and function. Also, the oxidizing reaction that causes microorganism inactivation does not form trihalomethanes (THMs) or haloacetic acids (HAAs).

Approvals and registrations for use of chlorine dioxide in a wide variety of applications have been granted by the EPA, FDA and USDA, and such approvals and registrations have led to an increasing adoption of the use of chlorine dioxide.

There are many reasons for the ongoing expansion of chlorine dioxide use including its effectiveness against microorganisms at very low concentrations.

A major limitation to the use of chlorine dioxide is that chlorine dioxide can not be manufactured in bulk at an industrial gas plant and shipped to final use destinations. Accordingly, chlorine dioxide must be generated on-site.

The use of chlorine dioxide in large scale applications is well known, however, the use of chlorine dioxide in small scale applications has not been widely adopted. The lack of adoption in small scale applications is a result of the limitations in the prior art with respect to the cost, speed, size and user-friendly generation of chlorine dioxide in sufficient concentration and purity to be useful. However, there are many small scale applications that would benefit from the use of chlorine dioxide as a deodorizing, disinfecting or sanitizing agent.

The present invention provides methods, apparatus and systems for generating and dispensing chlorine dioxide that are fast, low-cost, effective, compact and simple to use, thus remedying the deficiencies and limitations posed by the prior art which have impeded adoption for small scale uses.

The present invention will result in the increased adoption and use of this effective anti-microbial agent, with significant economic and health benefits to society.

SUMMARY OF THE INVENTION

The instant invention provides apparatus and methods for on-site generation of small volumes of chlorine dioxide gas. The invention has a number of aspects and embodiments which will be described below.

In one aspect, the invention provides apparatuses for the generation of gas comprising a reaction chamber comprising a first chamber, an inlet to the first chamber, a second chamber, and outlet from the second chamber, and an interface between the first and second chamber where the interfaces provides for the contents of the first chamber to enter the second chamber at a desired time.

In another embodiment the inlet comprises a unidirectional flow control, e.g., a check valve, where the unidirectional flow control retains the contents of the reaction chamber inside the reaction chamber.

In another embodiment the inlet comprises a membrane that is mechanically, or by another means, ruptured when the reaction chamber is inserted into the generator. In another embodiment the inlet comprises a membrane that is ruptured by a change in pressure. In another embodiment the inlet comprises a septum that is punctured when the reaction chamber is inserted in to the generator where the septum retains the contents of the reaction chamber. In a related embodiment the septum reseals after the puncturing element is removed from the septum.

In another embodiment the outlet comprises a check valve where the check valve retains the contents of the reaction chamber inside the reaction chamber. In another embodiment the outlet comprises a membrane that is mechanically ruptured when the reaction chamber is inserted into the generator. In another embodiment the outlet comprises a membrane that is ruptured by a change in pressure. In another embodiment the outlet comprises a septum that is punctured when the reaction chamber is inserted into the generator where the septum retains the contents of the reaction chamber inside the reaction chamber. In a related embodiment the septum reseals after the puncturing element is removed from the septum.

In another embodiment the interface between the first and second chamber is a check valve. The contents of the first chamber can pass through the interface to react with the contents of the second chamber when the reaction chamber is pressurized.

In another embodiment the interface is a membrane that opens or ruptures under pressure. In another embodiment the interface is a membrane that is mechanically ruptured when the reaction chamber is inserted into a generator.

In another embodiment the first chamber comprises water and the second chamber comprises a chlorite salt and an acid. In a related embodiment the chlorite salt and acid are in loose form. In a related embodiment the chlorite salt and acid are separated by a dissolvable structure. In another embodiment, the dissolvable structure is comprised of polyvinyl alcohol. In another related embodiment the chlorite salt and acid are physically separated. In another related embodiment the chlorite salt and acid are in separate structures. In another related embodiment the chlorite salt is in aqueous form. In another related embodiment the acid is in aqueous form.

In another embodiment the first chamber comprises an acid and the second chamber comprises a chlorite salt.

In another embodiment the first chamber comprises a chlorite salt and the second chamber comprises an acid.

In another embodiment the first chamber comprises water and a chlorite salt and the second chamber comprises and acid. The acid may be a liquid or a solid.

In another embodiment the first chamber comprises water and an acid and the second chamber comprises a chlorite salt. The chlorite salt may be a solid or dissolved in a liquid.

In various embodiments the chlorite salt is sodium chlorite, lithium chlorite, barium chlorite, calcium chlorite, magnesium chlorite, or potassium chlorite. In a specific embodiment, the chlorite salt is sodium chlorite.

In various embodiments, the acid is selected from the group consisting of boric acid, tartaric acid, lactic acid, maleic acid, malic acid, glutaric acid, adipic acid, acetic acid, formic acid, sulfamic acid, sulfuric acid, hydrochloric acid, phosphoric acid, phosphoric anhydride, sulfuric anyhdride and citric acid. In a specific embodiment, the acid is citric acid.

In various embodiments, the reaction chambers contain one hundredth, one tenth, one, two, ten or one hundred times the amount, e.g., the weight or volume, of citric acid as compared to sodium chlorite.

In another embodiment the reaction chamber comprises a neutralizing agent. The neutralizing agent reacts with the generated chemicals to form a more desirable byproduct, e.g., a less toxic, preferably a nontoxic, byproduct. In exemplary embodiments the neutralizing agent is an ascorbate salt, sodium thiosulfate, sodium sulfite or potassium sulfite. In a further specific embodiment the ascorbate salt is sodium ascorbate.

In another embodiment the neutralizing agent is in a dissolvable structure. In a related embodiment the dissolvable structure is designed to release the neutralizing agent some time after the reaction chamber has been activated.

In another embodiment, the dissolvable structure is comprised of polyvinyl alcohol.

In another embodiment the neutralizing agent is released mechanically at a desired time.

In another embodiment the reaction chamber is sized and shaped to allow the liquids in the chambers to freeze without damaging the reaction chamber or components of the reaction chamber. Such an embodiment will accommodate ice formation, which may occur during the transportation or storage of the reaction chamber. Geometries that are not damaged when the internal liquids freeze are well known in the art.

In another embodiment the liquid comprises an additive which inhibits the formation of contiguous pieces of ice. Such an additive will desirably cause the solution to freeze as slush rather than a uniform solid. In another embodiment the liquid comprises an additive which decreases the freezing temperature of the liquid.

In another embodiment the reaction chamber comprises a dispersal device for creating bubbles. The bubbles increase the transfer of gas from a solution to the outlet. The bubbles may also mix the contents of the reaction chamber.

In another embodiment the reaction chamber comprises a material having low water permeability. In a specific embodiments the low permeability material is a metal, polypropylene, PET, or polyethylene, or combinations thereof.

In another embodiment the reaction chamber comprises a fragrance. For example, it may be desirable to disperse a fragrance during or after an area has been treated with the generator. In a related embodiment the reaction chamber comprises a third chamber which comprises a fragrance. Additionally or alternatively fragrance(s) may be included in the first or second chambers.

In another embodiment the reaction chamber comprises a substance which changes color in the presence of a gas, for example, chlorine dioxide. The change in color may be used to indicate the presence of a the gas. In a specific embodiment the substance changes color in the presence of chlorine dioxide.

In another embodiment the reaction chamber comprises a substance which changes color in the presence of a neutralizing agent. The change in color may be used to indicate that the gas has been neutralized and only the desired byproducts remain. The reaction chamber may also include a colored neutralizing agent and/or a neutralizing agent which produced a colored byproduct upon neutralizing the gas (e.g. chlorine dioxide).

In another embodiment the reaction chamber further comprises a means for the generator to identify the reaction chamber. The reaction chamber may be identified optically. The optical detection may be by bar code, optical reflection, or optical transmission. The reaction chamber may be detected mechanically. The mechanical detection may be by switch. The reaction chamber may be detected magnetically. The magnetic detection may be by hall effect sensor.

In another aspect, the invention provides apparatuses for the generation of gas comprising a generator, an air flow source, a fitting connecting the airflow source to the inlet and a reaction chamber comprising a first chamber, an inlet to the first chamber, a second chamber, and outlet from the second chamber, and an interface between the first and second chamber where the interfaces provides for the contents of the first chamber to enter the second chamber. The gas generation chamber may generate chlorine dioxide in some embodiments.

In another embodiment the first chamber comprises water and the second chamber comprises a chlorite salt and an acid.

In a related embodiment the chlorite salt and acid are in loose form. In a related embodiment the chlorite salt and acid are separated by a dissolvable structure. In another embodiment, the dissolvable structure is comprised of polyvinyl alcohol. In another related embodiment the chlorite salt and acid are physically separated. In another related embodiment the chlorite salt and acid are in separate structures. In another related embodiment the chlorite salt is in aqueous form. In another related embodiment the acid is in aqueous form.

In another embodiment the first chamber comprises an acid and the second chamber comprises a chlorite salt.

In another embodiment the first chamber comprises a chlorite salt and the second chamber comprises an acid.

In another embodiment the first chamber comprises water and a chlorite salt and the second chamber comprises and acid. The acid may be a liquid or a solid.

In another embodiment the first chamber comprises water and an acid and the second chamber comprises a chlorite salt. The chlorite salt may be a solid or dissolved in a liquid.

In various embodiments the chlorite salt is sodium chlorite, lithium chlorite, barium chlorite, calcium chlorite, magnesium chlorite, or potassium chlorite. In a specific embodiment, the chlorite salt is sodium chlorite.

In various embodiments, the acid is selected from the group consisting of boric acid, tartaric acid, lactic acid, maleic acid, malic acid, glutaric acid, adipic acid, acetic acid, formic acid, sulfamic acid, sulfuric acid, hydrochloric acid, phosphoric acid, phosphoric anhydride, sulfuric anyhdride and citric acid. In a specific embodiment, the acid is citric acid.

In various embodiments, the reaction chambers contain one hundredth, one tenth, one, two, ten or one hundred times the amount, e.g., the weight or volume, of citric acid as compared to sodium chlorite.

In another embodiment the reaction chamber comprises a neutralizing agent. The neutralizing agent reacts with the generated chemicals to form a more desirable byproduct, e.g., a less toxic, preferably a nontoxic, byproduct. In a specific embodiment the neutralizing agent is an ascorbate salt, sodium thiosulfate, sodium sulfite or potassium sulfite. In a further specific embodiment the ascorbate salt is sodium ascorbate.

In another embodiment the neutralizing agent is in a dissolvable structure. In a related embodiment the dissolvable structure is designed to release the neutralizing agent some time after the reaction chamber has been activated.

In another embodiment, the dissolvable structure is comprised of polyvinyl alcohol.

In another embodiment the neutralizing agent is released mechanically at a desired time.

In another embodiment the reaction chamber is sized and shaped to allow the liquids in the chambers to freeze without damaging the reaction chamber or components of the reaction chamber. Such an embodiment will accommodate ice formation, which may occur during the transportation or storage of the reaction chamber. Geometries that are not damaged when the internal liquids freeze are well known in the art.

In another embodiment the liquid comprises an additive which inhibits the formation of contiguous pieces of ice. Such an additive will desirably cause the solution to freeze as slush rather than a uniform solid. In another embodiment the liquid comprises an additive which decreases the freezing temperature of the liquid.

In another embodiment the reaction chamber comprises a dispersal device for creating bubbles. The bubbles increase the transfer of gas from a solution to the outlet. The bubbles may also mix the contents of the reaction chamber.

In another embodiment the reaction chamber comprises a material having low water permeability. In a specific embodiment the low permeability material is a metal, polypropylene, PET, or polyethylene, or combinations thereof.

In another embodiment the reaction chamber comprises a fragrance. For example, it may be desirable to disperse a fragrance during or after an area has been treated with the generator. In a related embodiment the reaction chamber comprises a third chamber which comprises a fragrance. Additionally or alternatively fragrance(s) may be included in the first or second chambers.

In another embodiment the reaction chamber comprises a substance which changes color in the presence of a gas, for example, chlorine dioxide. The change in color may be used to indicate the presence of a the gas. In a specific embodiment the substance changes color in the presence of chlorine dioxide.

In another embodiment the reaction chamber comprises a substance which changes color in the presence of a neutralizing agent. The change in color may be used to indicate that the gas has been neutralized and only the desired byproducts remain. The reaction chamber may also include a colored neutralizing agent and/or a neutralizing agent which produced a colored byproduct upon neutralizing the gas (e.g. chlorine dioxide).

In another embodiment the reaction chamber further comprises a means for the generator to identify the reaction chamber. The reaction chamber may be identified optically. The optical detection may be by bar code, optical reflection, or optical transmission. The reaction chamber may be detected mechanically. The mechanical detection may be by switch. The reaction chamber may be detected magnetically. The magnetic detection may be by hall effect sensor.

In another embodiment the generator comprises a regulator for controlling the flow of air from the air flow source into the reaction chamber inlet.

In another embodiment the generator comprises a water source. The water may be used to generate the gas in the reaction chamber.

In another embodiment the fitting comprises an o-ring.

In another embodiment the generator comprises a sensor from group consisting of: a gas concentration sensor, a chlorine dioxide sensor, a temperature sensor for sensing the outlet temperature of the gases, a relative humidity (% RH) sensor and a temperature sensor for sensing the ambient temperature.

In another embodiment the system stops the air flow if the sensor reports a value beyond a threshold. In a related embodiment the system adjusts the air flow if the sensor reports a value beyond a threshold. In another related embodiment the system adjusts the duration of air flow if the sensor reports a value beyond a threshold. In another related embodiment the system adjust the air temperature based on a value generated by the sensor.

In an related embodiment, the sensor activates a visual or audible alarm when it is safe to enter a treated area. Alternatively, the sensor activates a visual or audible alarm when it is unsafe to enter an area that is being treated. In a another embodiment, the sensor alerts a user when the chlorine dioxide level has reached a level that it is safe to reenter the area in which the instrument is being used. The same sensor may be connected to other safety mechanisms, modalities or features.

In a another embodiment, the sensor alerts a user when the chlorine dioxide level has reached a level that it is same to reenter the area in which the instrument is being used. In an exemplary embodiment, the sensor allows for the reentry to a given area by physically unlocking a door, thereby allowing individuals to reenter the disinfected or deodorized area.

In another embodiment the generator comprises a heater for heating the air before entry into the reaction chamber.

In another embodiment the generator comprises a neutralizing agent dispersal means.

In another embodiment the generator comprises a light source. Certain gases, particularly chlorine dioxide, can be neutralized by exposure to a light source. In a related embodiment the light source is an ultraviolet light.

In another embodiment the generator comprises an air filter for removing the generated gas from ambient gas, possibly a room or a test chamber. In a related embodiment the filter comprises activated carbon.

In another embodiment the reaction chamber comprises a mixer and the generator comprises a driver for actuating the mixer. In a related embodiment the energy is magnetically transferred from the driver to the mixer. In another related embodiment the driver and the mixer are mechanically coupled. In another embodiment the reaction chamber comprises a mixer driven by air flow from the inlet.

In some embodiments, the system includes an external sensor for detecting a concentration of a gas, for example, chlorine dioxide. The external sensor may or may not be in communications with the regulator.

In other embodiments, the system may include a detachable display. The system may be configured to begin gas generation at a defined interval from the removal of the detached display from the system. The detachable display may indicate an amount of time remaining in the gas generation cycle.

In another embodiment the generator comprises an gas dispersal means for distributing a gas in the air around the generator. In another embodiment the gas dispersal means is a fan or a mister.

In another embodiment the generator is portable.

In another aspect, the invention provides apparatuses for the generation of a gas, e.g., chlorine dioxide. This apparatus comprises a water source, a reaction chamber (as described herein), and a fitting. The reaction chamber includes an inlet, an outlet, and dry precursor chemicals. The fitting connects the water source to the inlet.

In further embodiments, the system includes a water filter connected to the water source and the inlet. The system may also include a water heater for heating water received from the water source.

DETAILED DESCRIPTION OF THE INVENTION

The instant invention provides apparatus for the generation of gas, including but not limited to chlorine dioxide, in a variety of small volumetric applications and concentrations for such applications, including, but not limited to: food dispensing services, food preparation equipment, dental equipment, medical equipment, medical facilities, recreational vehicles, boats, emergency disinfection needs, deodorizing, and many other uses.

The present invention provides easy-to-use, low-cost methods, devices and systems for the generation of chlorine dioxide. In some embodiments, the apparatus of the invention can generate concentration of chlorine dioxide from 0.05 parts per million (PPM) to 5,000 PPM, typically from 0.1 PPM to 500 PPM in a desired volume. In specific embodiments of the invention, the reaction chamber contains 0, 1, 20, 50, 100, 500, 1000, 5000 milliliters of aqueous solution in which the chlorine dioxide is generated. The apparatus of the invention generates the chlorine dioxide in between 0 and 60 minutes, having a desired volume and concentration.

The chlorine dioxide generated may be used for deodorizing, disinfecting or sanitizing purposes depending on specific disinfection or sanitization requirements.

Figure 1:
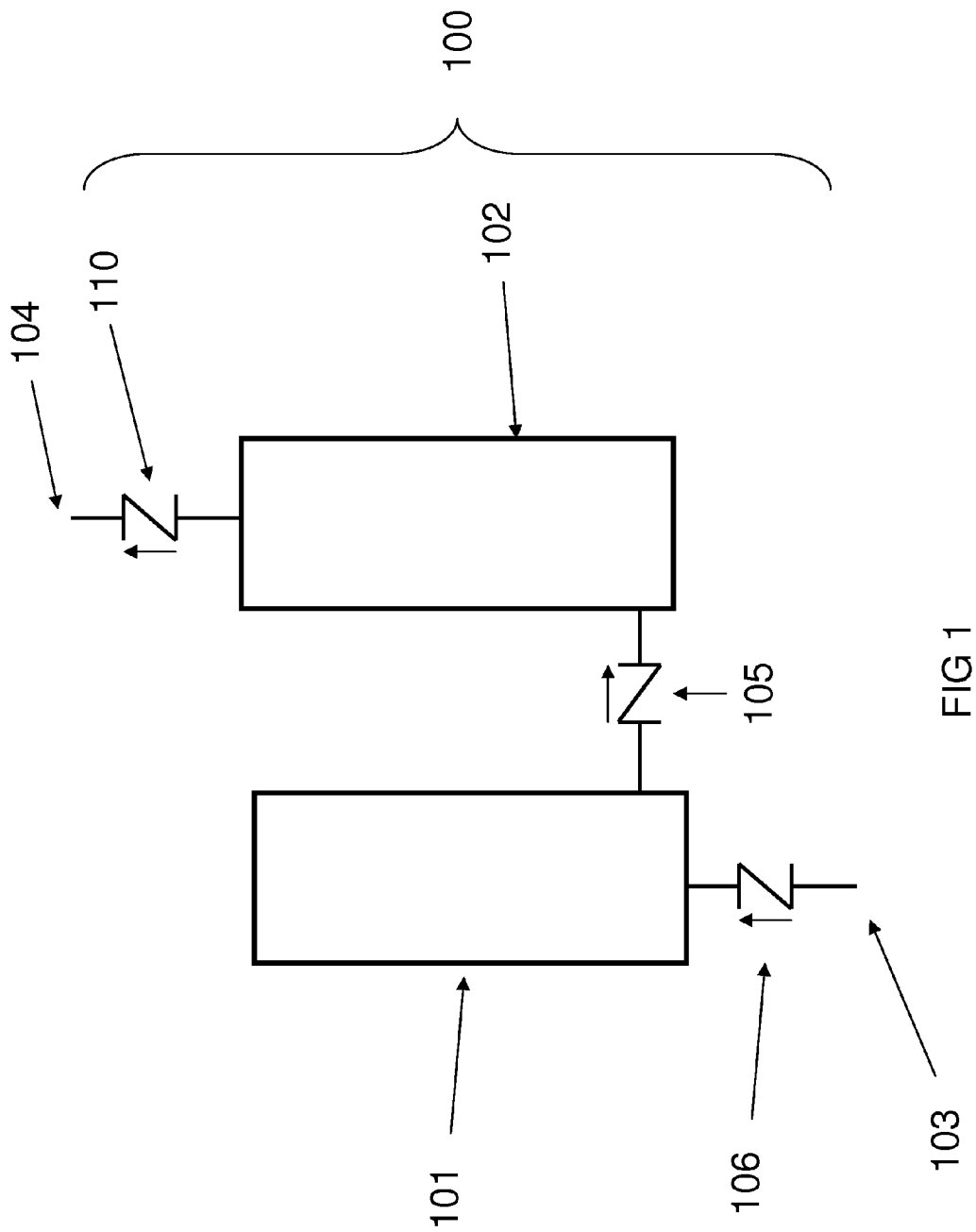
FIG. 1 is a schematic representation of one embodiment of a reaction chamber according to the invention.

FIG. 1 is not shown to scale and is not intended to show spatial relationships or components. Further, the components depicted in FIG. 1 may be connected by one of ordinary skill in the art using appropriate connections, tubing and the like, so as to function as described herein.

FIG. 1 depicts an embodiment of reaction chamber 100. In particular embodiments one precursor chemical in aqueous solution is contained in first chamber 101 and a second precursor chemical is contained in second chamber 102. The chemicals are separated from each other by interface 105. In certain embodiments interface 105 comprises a unidirectional flow device, e.g., a check valve. Alternative embodiments of interface 105 include, but are not limited to, a membrane that is ruptured on activation by increased pressure, or a mechanical interface that is opened when reaction chamber 100 is inserted in generator 200.

In certain embodiments inlet 103 to first chamber 101 may include check valve 106. Check valve 106 serves to keep the contents of first chamber 101 inside reaction chamber 100 when reaction chamber 100 is removed from generator 200. Alternative embodiments include, but are not limited to, inlet 103 comprising a membrane that is ruptured on activation by increased pressure, a membrane that is mechanically ruptured when reaction chamber 100 is inserted in generator 200, a membrane that is mechanically ruptured by the operator, or a septum that is pierced by a needle and may reseal when the needle is removed.

In certain embodiments outlet 104 to second chamber 102 may comprise check valve 110. The cracking pressure of check valve 110 serves to keep the contents of second chamber 102 inside reaction chamber 100. Alternative embodiments include, but are not limited to, outlet 103 comprising a membrane that is ruptured on activation by increased pressure, a membrane that is mechanically ruptured when reaction chamber 100 is inserted in generator 200, a membrane that is mechanically ruptured by the operator, or a septum that is pierced by a puncturing element and may reseal when the puncturing element is removed.

In one embodiment, the water is not allowed to flow out of the second chamber.

In preferred embodiments, the precursor chemicals are contained within reaction chamber 100 with one chemical in solution in first chamber 101 and a second chemical, dry or liquid, in second chamber 102. In this way the interface keeps the chemicals separated after production of the reaction chamber until the reaction chamber is activated. However, one of skill in the art will realize that alternative embodiments exist. Precursor chemicals may be in dry form or aqueous form in first chamber 101 or second chamber 102. Precursor chemicals may be in the same chamber in numerous ways/methods to include but not limited to the following methods: dry powder form; dry powder mixed together in a tea-bag structure; dry powder separated into two tea-bag structures; dry powder separated into two membrane structures; dry powder mixed together in a dissolvable (water soluble) film bag; dry powder separated into two dissolvable (water soluble) film bags; dry powder mixed together in a dissolvable (water soluble) gel tablet; dry powder separated into two dissolvable (water soluble) gel tablets; dry powder separated into two dry pills. In cases where a precursor chemical containing structure is made from a hydrophilic heat-sealable material, such material may be made with a sufficiently small pore size that it will provide some containment of undesirable residuals.

In alternate embodiments, reaction chamber 100 may contain one or more internal structural components that function to hold the precursor chemicals in a specific orientation within reaction chamber 100. In this embodiment only a precursor chemical containing structure is disposable, and a new precursor chemical containing structure is used for each reaction cycle. For example, first chamber 101 and second chamber 102 may be inserted separately into generator 200. The required connections to facilitate the flow of a precursor chemical from first chamber 101 to second chamber 102. In other embodiments, first chamber 101 and second chamber may be mechanically or chemically bonded, but still without an internal connection between first chamber 101 and second chamber 102. Such embodiments could potentially lower the per unit cost of reaction chambers.

In certain embodiments precursor chemicals are an acid and a chlorite salt. Exemplary chlorite salts are sodium chlorite, lithium chlorite, barium chlorite, calcium chlorite, magnesium chlorite, or potassium chlorite. Exemplary acids are boric acid, tartaric acid, lactic acid, maleic acid, malic acid, glutaric acid, adipic acid, acetic acid, formic acid, sulfamic acid, sulfuric acid, hydrochloric acid, phosphoric acid, phosphoric anhydride, a sulfuric anyhdride and citric acid. An exemplary chlorite salt/acid combination used in the apparatus of the invention is sodium chlorite and citric acid.

One of ordinary skill in the art understands that adjusting the ratio of the acid and chlorite salt will allow for the variation and control of the speed of the reaction and the amount of chlorine dioxide produced. Exemplary ratios of acid:chlorite salt are: 100:1, 10:1, 2:1, 1:1, 10:1, 100:1 or any fractional ratio within the exemplified range.

In certain embodiments the reaction chamber may contain a chemical for neutralizing a reaction or the products of a reaction. In the preferred embodiment an ascorbate salt, for example sodium ascorbate, is released in second chamber 102, where it reacts with the residual chlorine dioxide neutralizing it. In certain cases it may be desirable to neutralize various chemicals in the reaction chamber, either to control the reaction rate or to make reaction chamber 100 easier to dispose of or safer to handle. For example, sodium ascorbate will react with chlorine dioxide to produce products which are more readily disposed of than chlorine dioxide. In certain embodiments the neutralizing agent may have a detectable color.

The neutralizing agent may be stored in reaction chamber 100, generator 200, or another source such as a tank or piping system. If a neutralizing agent is used, it is important to control the release of the neutralizing agent. The release of the neutralizing agent release may be controlled by retaining the neutralizing agent in a dissolvable membrane structure where the membrane dissolves after some time releasing the neutralizing agent. An example of a dissolvable membrane is polyvinyl alcohol. The neutralizing agent may also be mechanically released, for example a certain time after the reaction begins, once the chlorine dioxide concentration reaches a defined threshold, or once a defined chlorine dioxide concentration is maintained for a defined period of time.

In certain embodiments the geometry of reaction chamber 100 may be shaped or sized so that if the reaction chamber is exposed to cold temperature expansion from the freezing solution will not cause damage to reaction chamber 100 or its elements. One skilled in the art will be able to prevent damage from freezing in a variety of ways, including, but not limited to, allowing extra space for the frozen solid to expand into, or enclosing the solution in a flexible chamber that can stretch without damage as the solution freezes.

In certain embodiments the reaction chamber may be protected from freezing by certain additives to the solutions. Additives may be used to decrease the freezing temperature of the solutions or to change the frozen solution from a uniform solid which may damage the reaction chamber to a slush which will not damage reaction chamber 100.

In certain embodiments the reaction chamber may be made of a material having low permeability. After long term storage of reaction chambers 100 may need to maintain sufficient water for reaction. In other embodiments the reaction chamber may be enclosed in another chamber, for example a foil or metalized Mylar bag, which would have low water permeability.

The reaction chamber may contain machine readable identification information to ensure that the reaction chamber is appropriate for a generator. Relevant identification may include serial number, product number, date of manufacture, expiration date, and/or product class. Identifications information may be stored in transmitted in a variety of ways known to those of skill in the art. For example, identification information may be encoded as a bar code or other optical code or may be encoded in memory or a microprocessor chip.

In certain embodiments of reaction chamber 100, a fragrance may be included. The fragrance may be mixed with the precursor chemicals in first chamber 101 or second chamber 102 or it may be a third chamber. The fragrance may be contained in its own structure than is mechanically ruptured or is dissolvable. The fragrance may be released prior to, at the same time of, or after the gas generation cycle. The fragrance may be a dry chemical, an oil, or a soluble chemical.

In certain embodiments the reaction chamber may include a substance that changes color in the presence of a gas, for example chlorine dioxide gas.

In certain embodiments the reaction chamber may include a substance that changes color in the presence of a neutralizing agent, for example sodium ascorbate.

The apparatus of the invention will need power to operate. Possible power sources include, but are not limited to 230 voltAC, 115 voltAC, 24 voltDC, 12 voltDC, 9 voltDC, 6 voltDC, or 3 voltDC. The apparatus may also be adapted to draw electricity from batteries produced for cordless power tools, allowing for demolition contractors to disinfect unsanitary areas, for example houses flooded with sewage during Hurricane Katrina. An advantage of this device is that certain embodiments use little power and may easily be battery powered increasing the portability and ease of use of the device.

Figure 2:
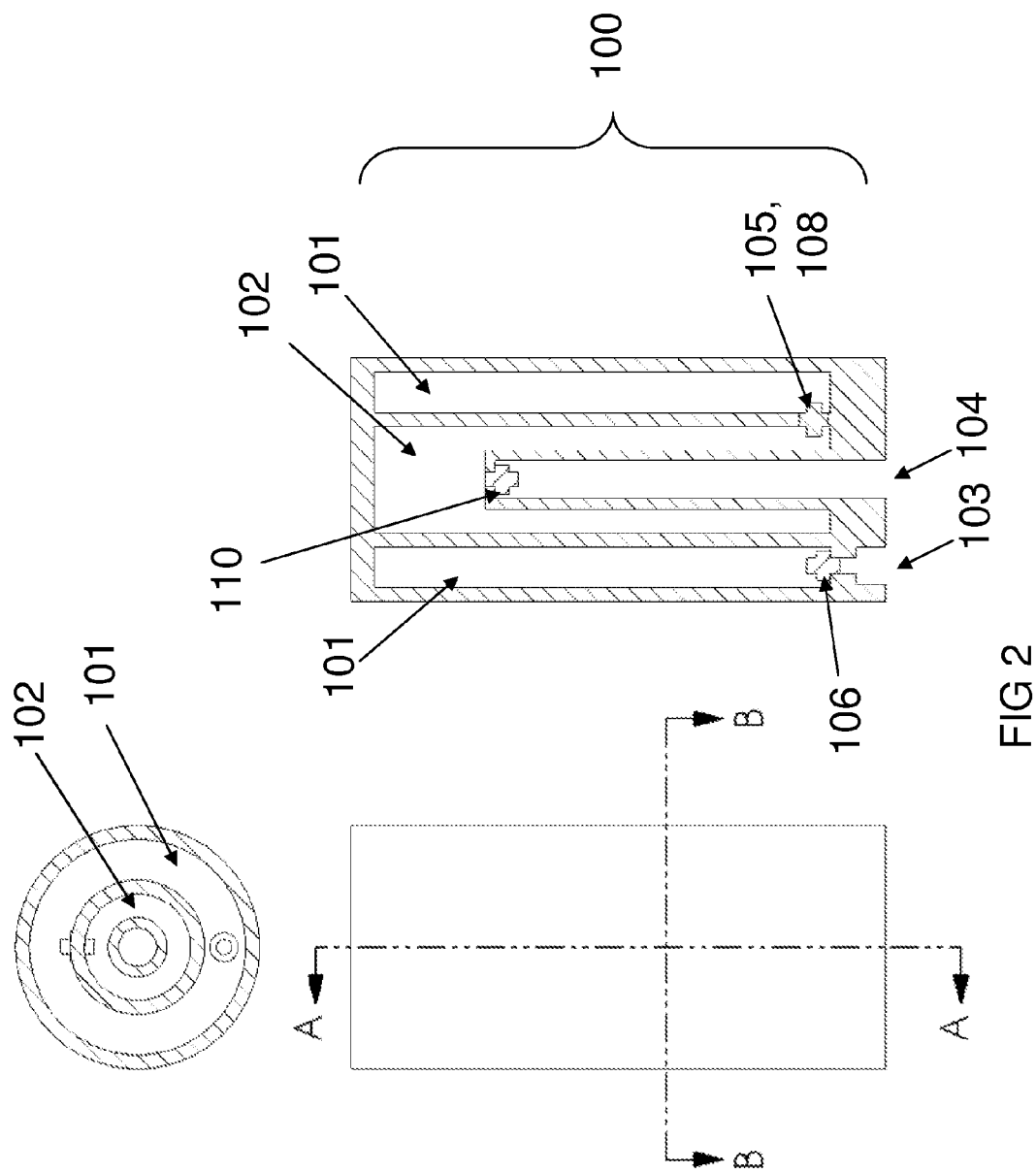
FIG. 2 is a drawing and section of one embodiment of a reaction chamber according to the invention.

FIG. 2 depicts an embodiment of reaction chamber 100 that uses a check valve 106 at inlet 103, interface 105, and check valve 110 at outlet 104.

Figure 3:
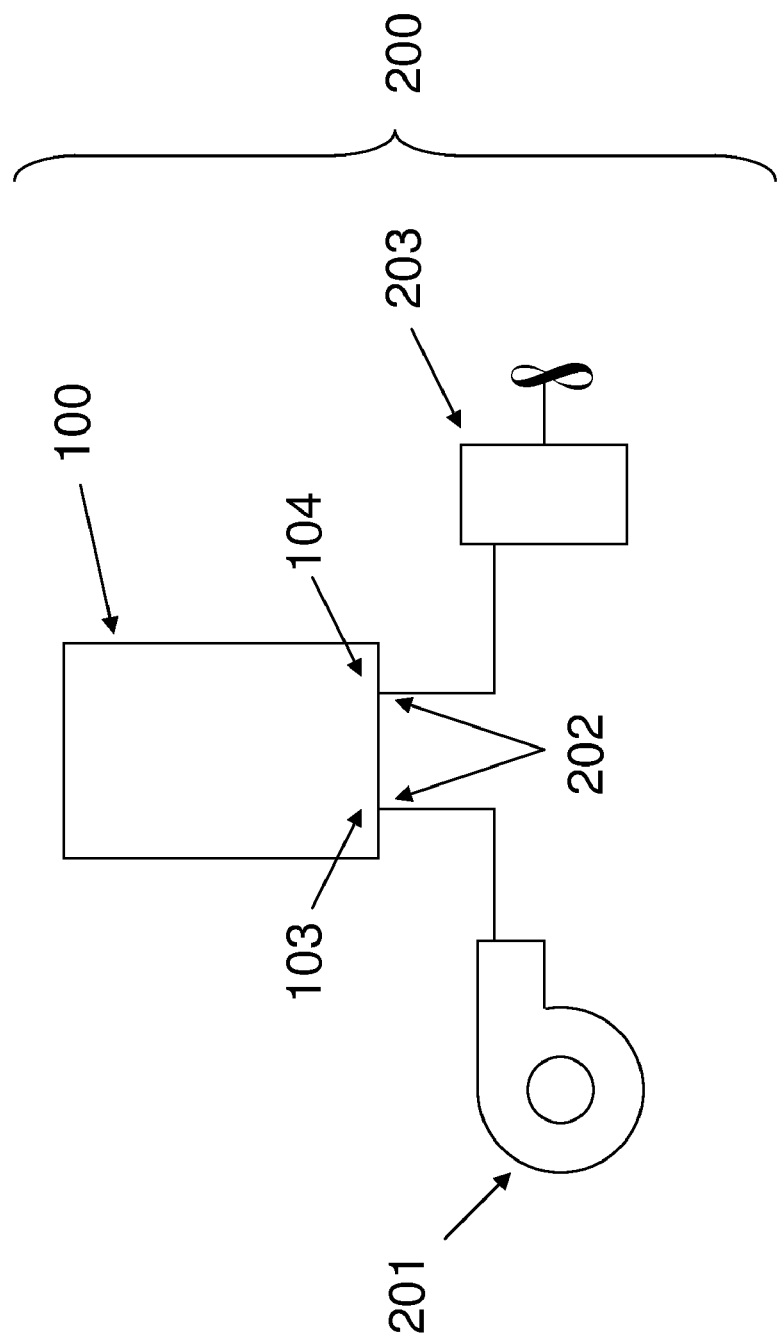
FIG. 3 is a schematic representation of one embodiment of the invention.

FIG. 3 is not shown to scale and is not intended to show spatial relationships or components. Further, the components depicted in FIG. 3 may be connected by one of ordinary skill in the art using appropriate connections, tubing and the like, so as to function as described herein.

Reaction chamber 100 is inserted in generator 200. In certain embodiments there is a fitting 202 which connects the air pump 201 to inlet 103. The fitting may include an o-ring seal, friction seal, or other means for connecting the air pump 201 to the reaction chamber. The term "fitting" refers broadly to any means or apparatus for connecting a cartridge or chamber to a pipe, tube, or other fluid or gas carrying system. For example, "fittings" include systems tubing or piping is connected direct to an inlet, outlet, or other interface on reaction chamber 100. Outlet 104 may release the gas directly out in to the space intended to be exposed the generated gas. In certain embodiments, outlet 104 may include a fitting to deliver the air to the fan 203.

In certain embodiments an air pump 201 is used as the air source. After reaction chamber 100 is inserted in generator 200, the air source generates a pressure in first chamber 101 which drives the contents of first chamber 101 in to second chamber 102 and initiates the gas generation reaction. In the preferred embodiment, chlorine dioxide gas is generated in second chamber 102, and the air source continues to bubble air through the solution in second chamber 102 releasing chlorine dioxide from the solution which can then travel out outlet 104 in to the space surrounding generator 200. In certain embodiments, a bubble dispersing device, for example a porous frit, may be used to increase the mixing, change the reaction rates or change the rate at which the gas leaves second chamber 102. In certain embodiments, fan 203 may be used to disperse the chlorine dioxide or to make a more uniform concentration of chlorine dioxide within a space.

In certain embodiments generator 200 includes a regulator for adjusting the air flow. The regulator may be a pressure regulator or a valve. In other embodiments generator 200 includes a control from switching the air source on and off repeatedly to control the air flow. The regulator may be configured to adjust air flow on the basis of time, concentration of chlorine dioxide, and/or input from an internal or external sensor.

In certain embodiments generator 200 may contain a water source, such as a refillable tank. The water could then be routed to the reaction chamber to initiate the gas generating reaction. In an alternate embodiment generator 200 could be connect to a water supply system. In related embodiments the generator may have a filter, a heater or other means for adjusting the properties of the water entering the reaction chamber. Connection to a water source may be any fitting that allows for quick and easy connection to a water source. Exemplary fittings include threaded fittings and quick-connect type fittings to which a water source can be connected to and subsequently removed. In one embodiment, the water fills a tank prior to the reaction starting. Upon the starting of the apparatus, a pre-measured amount of water is released or pumped from the water tank into the reaction chamber, thereby allowing for the reaction to commence.

Figure 4:
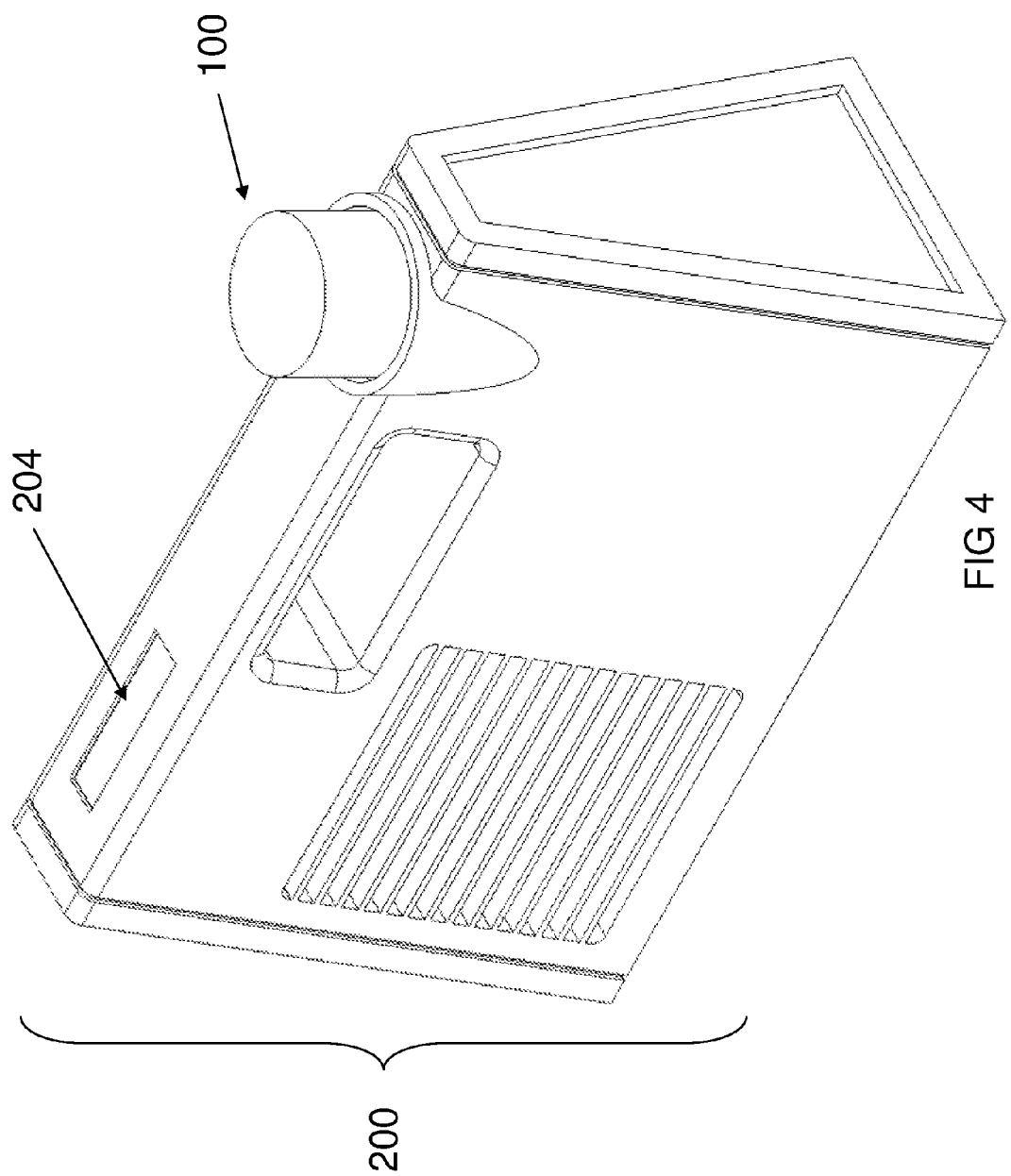
FIG. 4 is a drawing of one embodiment of a generator according to the invention.

FIG. 4. depicts an embodiment of portable gas generator 200. Display 204 is shown for communicating to the user. Information that may be communicated includes, but is not limited to, the state of the generation cycle, the chlorine dioxide concentration, information gathered by various sensors, or the time of operation.

In certain embodiments generator 200 may contain various sensors. The sensors may include but are not limited to temperature sensors, relative humidity sensors, or gas concentration sensors, for example chlorine dioxide sensors.

In certain embodiments the information from the sensor may be used to control the air flow rate or the air flow time to adjust the rate of reaction or rate of gas production. In this way it is possible to generate a specific concentration profile around generator 200 using sensor feedback. In certain embodiments temperature control may be used to control the rate of reaction or gas production. In generator 200, a heater may be used to warm the air before it enters reaction chamber 100. The amount of heating may be determined from a sensor reading.

In certain embodiments the generator may stop operation when a sensor reaches a certain value. For example, the air source may stop blowing when a chlorine dioxide sensor reaches a threshold value.

In certain embodiments generator 200 may have a way to neutralize the gas in the surrounding area. For example, to neutralize chlorine dioxide the system may shine a light source, possibly an ultraviolet light source, or expose the chlorine dioxide to a filter, possibly an activated carbon filter, or disperse another reactive chemical in to the air, possibly as a fog or gas. The generator may include neutralizing agent dispersal means as well known to those of skill in the art. Examples of neutralizing agent means include atomizers, carburetors, misters, nozzles, pumps, fans, impellers, injectors, foggers, orifice plates, aerosol devices, and the like. Neutralizing the gas would allow for more controlled exposure times and faster exposure times in gas treatment applications.

In certain embodiments generator 200 has a means for mixing the solutions in reaction chamber 100. For example the mixing may take place by one or more of the following: agitation from the air flow, a mechanical mixer driven by the air flow, a mechanical mixer mechanically coupled to the generator, a mechanical mixer magnetically coupled to the mixer.

In certain embodiments, the generator comprises gas dispersal means for distributing a gas in the air around the generator. Gas dispersal means include, but are not limited to, atomizers, carburetors, misters, nozzles, pumps, fans, impellers, injectors, foggers, orifice plates, aerosol devices, and the like.

In certain embodiments the generator may have a detachable display that communicates information about the gas generation cycle. For example it may time the length of the generation cycle, display the concentration of gas, or display a signal that it is safe or unsafe to enter the space with generator 200. The detachable display may completely disconnect from generator 200 or it may be tethered. The detachable display may be in wireless communication with generator 200 or other sensors.

In certain embodiments the detachable display may start the gas generation cycle a predetermined time after the detachable display has been removed from the generator. In this embodiment, the detachable display is independent from generator 200. This independence may be advantageous in an environment where radio interference hinders communication between display and generator 200 or in environment such as hospitals that impose restrictions on wireless communications.

Figure 5:
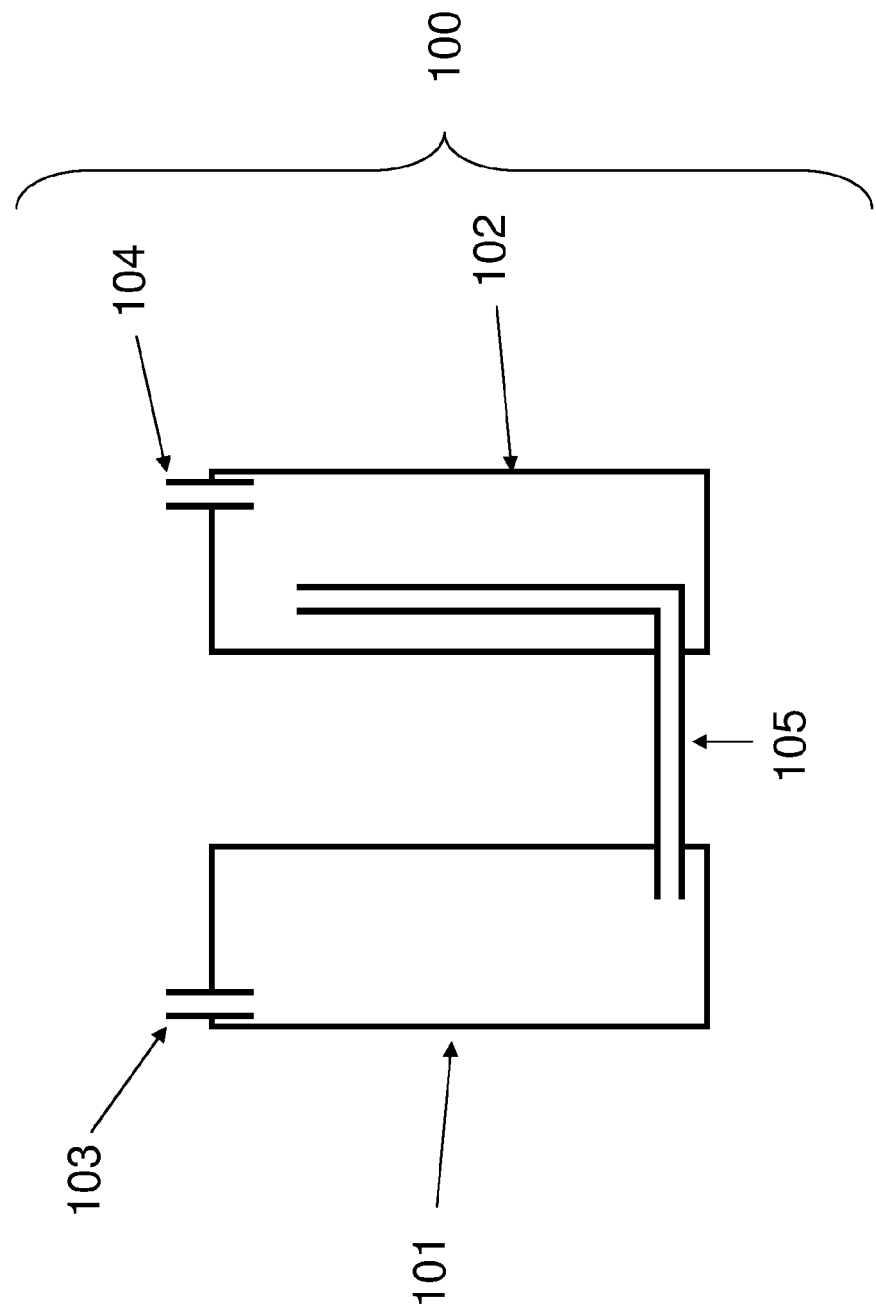
FIG. 5 represents an alternate embodiment of the invention.

FIG. 5 depicts an alternative embodiment of the invention. This embodiment does not use check valves or seals at inlet 103, outlet 104, or interface 105. The contents of first chamber 101 and second chamber 102 are separated by the geometry of the interface.

Figure 6:
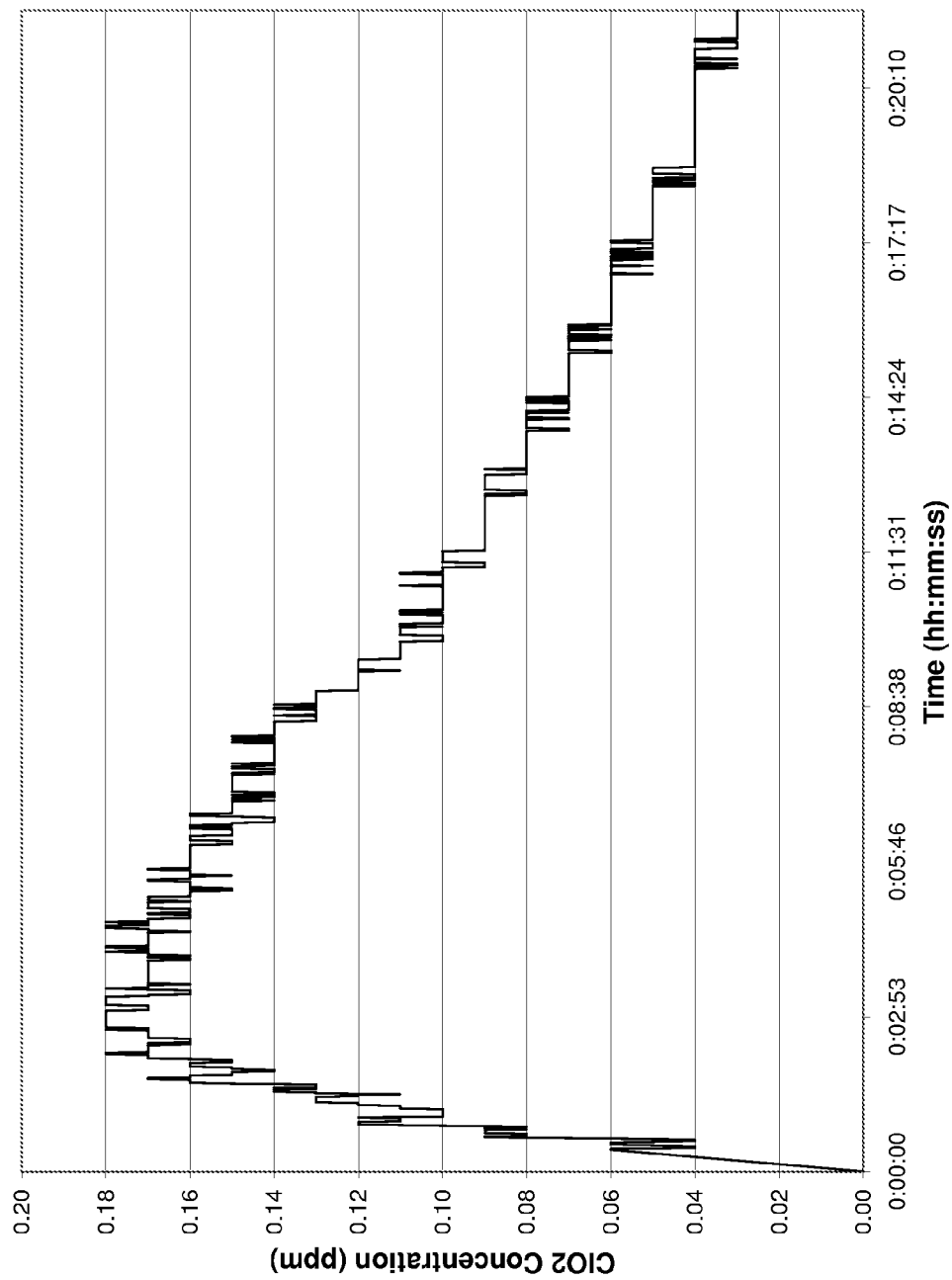
FIG. 6 is a graph depicting results of the embodiments shown in FIG. 1 and FIG. 3.

FIG. 6 shows the data from a typical run of the invention to generate chlorine dioxide. The fast rise in concentration and then decay is typical of the invention. Various modifications to the gas concentration profile could be made by controlling the reaction and air flow in various ways.

EXAMPLES

It should be appreciated that the invention should not be construed to be limited to the examples that are now described; rather, the invention should be construed to include any and all applications provided herein and all equivalent variations within the skill of the ordinary artisan.

Example 1

In this example the embodiment of the reaction chamber is that of FIG. 2 and the embodiment of the generator is that of FIG. 3. The reaction chamber was made from acrylic tubes with ABS end caps. The end caps were removable to allow access to the chambers and then re-sealable. Approximately 1.5 grams of sodium chlorite and 3.0 grams of citric acid were loaded as dry powders in second chamber 102. Approximately 25 ml of water was loaded in first chamber 101.

The generator was placed in the center of an 8 ft×8 ft×10 ft tall room. The HVAC ducts were blocked. The reaction chamber was place into generator 200. Generator 200 was run with a 12V power supply. A BW Gas Alert Extreme Model GAXT-V-DL chlorine dioxide sensor was placed on a small shelf on the side of the room.

A timer on the generator was set for approximately 8 minutes. The generator was turned on. The air pump generated pressure in first chamber 101 which drove the water through interface 105 check valve and started the reaction within second chamber 102. Second chamber 102 quickly turned yellow indicating the generation of chlorine dioxide. Air continued to bubble through second chamber 102 for the duration of the timer. Bubbled air carried generated chlorine dioxide out outlet 104 of reaction chamber 100 and through a tube to fan 203. The fan then distributed the chlorine dioxide around the room and avoided any build-up of undesirably high concentrations.

After approximately 8 minutes the timer stopped which automatically stopped the air pump and the fan. FIG. 5 shows the chlorine dioxide concentration recorded by the chlorine dioxide sensor. The concentration rose to a peak of 0.18 ppm in two minutes and then decayed to 0.04 ppm after 20 minutes.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the instant invention and the following claims.

What is claimed is:

1. A reaction chamber for the generation of a gas comprising:
   a first chamber;
   a second chamber;
   an interface between the first chamber and the second chamber, the interface allowing contents of the first chamber to enter the second chamber at a desired time; and
   a neutralizing agent stored in a dissolvable structure.

2. The reaction chamber according to claim 1 wherein the gas is chlorine dioxide.

3. The reaction chamber according to claim 1 further comprising:
   an inlet to the first chamber.

4. The reaction chamber according to claim 3 wherein the inlet comprises a check valve.

5. The reaction chamber according to claim 3 wherein the inlet comprises a membrane that is mechanically ruptured when the reaction chamber is inserted in a generator.

6. The reaction chamber according to claim 3 wherein the inlet comprises a membrane that is ruptured by a change in pressure.

7. The reaction chamber according to claim 3 wherein the inlet comprises a septum that is punctured when the reaction chamber is inserted in a generator.

8. The reaction chamber of claim 7, wherein the reaction chamber is resealable.

9. The reaction chamber according to claim 1 further comprising:
   an outlet from the second chamber.

10. The reaction chamber according to claim 9 wherein the outlet comprises a check valve.

11. The reaction chamber according to claim 9 wherein the outlet comprises a membrane that is mechanically ruptured when the reaction chamber is inserted in a generator.

12. The reaction chamber according to claim 9 wherein the inlet comprises a membrane that is ruptured by a change in pressure.

13. The reaction chamber according to claim 9 wherein the outlet comprises a septum that is punctured when the reaction chamber is inserted in a generator.

14. The reaction chamber of claim 13, wherein the reaction chamber is resealable.

15. The reaction chamber according to claim 1 wherein the interface is a check valve.

16. The reaction chamber according to claim 1 wherein the interface is a membrane that opens under pressure.

17. The reaction chamber according to claim 1 wherein the interface is a membrane that is mechanically ruptured when the reaction chamber is inserted in a generator.

18. The reaction chamber according to claim 1 wherein the first chamber comprises water and the second chamber comprises a chlorite salt and an acid.

19. The reaction chamber of claim 18, wherein the chlorite salt is selected from the group consisting of sodium chlorite, lithium chlorite, barium chlorite, calcium chlorite, magnesium chlorite, and potassium chlorite.

20. The reaction chamber of claim 18, wherein the chlorite salt is sodium chlorite.

21. The reaction chamber of claim 18, wherein acid is selected from the group consisting of boric acid, tartaric acid, lactic acid, maleic acid, malic acid, glutaric acid, adipic acid, acetic acid, formic acid, sulfamic acid, sulfuric acid, hydrochloric acid, phosphoric acid, phosphoric anhydride, a sulfuric anyhdride and citric acid.

22. The reaction chamber of claim 18, wherein the acid is citric acid.

23. The reaction chamber according to claim 18 wherein the chlorite salt and the acid are in a loose form.

24. The reaction chamber according to claim 18 wherein the chlorite salt and the acid are in a dissolvable membrane.

25. The reaction chamber according to claim 18 wherein the chlorite salt and the acid are physically separated.

26. The reaction chamber according to claim 18 wherein the sodium chlorite is stored in a first structure and the acid is stored in a second structure.

27. The reaction chamber according to claim 1 wherein the first chamber comprises water and acid, and the second chamber comprises a chlorite salt.

28. The reaction chamber according to claim 1 wherein the first chamber comprises water and a chlorite salt, and the second chamber comprises an acid.

29. The reaction chamber according to claim 28 wherein the acid is a liquid.

30. The reaction chamber according to claim 1 wherein the first chamber comprises an acid and the second chamber a chlorite salt.

31. The reaction chamber according to claim 1 wherein the first chamber comprises a chlorite salt and the second chamber comprises an acid.

32. The reaction chamber according to claim 1 wherein the neutralizing agent is an ascorbate salt.

33. The reaction chamber of claim 32, wherein the ascorbate salt is sodium ascorbate.

34. The reaction chamber according to claim 1 wherein the neutralizing agent is sodium sulfite.

35. The reaction chamber according to claim 1 wherein the neutralizing agent is sodium bisulfite.

36. The reaction chamber according to claim 1 wherein the reaction chamber accommodates ice formation within the reaction chamber.

37. The reaction chamber according to claim 1 further comprising:
    an air dispersal device for creating bubbles.

38. The reaction chamber according to claim 1 wherein the reaction chamber comprises a material having low water permeability.

39. The reaction chamber according to claim 1 further comprising:
a fragrance.

40. The reaction chamber according to claim 1 wherein the first chamber comprises a fragrance.

41. The reaction chamber according to claim 1 wherein the second chamber comprises a fragrance.

42. The reaction chamber according to claim 1, further comprising a colored neutralizing agent.

43. The reaction chamber according to claim 1, further comprising:
machine readable identification information.

44. A system for the generation of a gas comprising:
an air flow source;
a reaction chamber comprising:
  a first chamber;
  an inlet connected to the first chamber;
  a second chamber connected to the first chamber by an interface, the interface allowing contents of the first chamber to enter the second chamber at a desired time;
  a neutralizing agent stored in a dissolvable structure; and
  an outlet connected to the second chamber.

45. The system of claim 44, further comprising a fitting for connecting the air flow source to the inlet.

46. The system of claim 45, further comprising a regulator for controlling air flow.

47. The system of claim 44 wherein the gas is chlorine dioxide.

48. The system according to claim 44 further comprising:
a water source connected to the inlet, the water source providing water to the reaction chamber.

49. The system according to claim 45 wherein the fitting comprises an O ring.

50. The system according to claim 44 further comprising:
a sensor selected from the group consisting of: a gas concentration sensor, a chlorine dioxide sensor, a temperature sensor for sensing the temperature of the reaction chamber, a temperature sensor for sensing the outlet temperature of gas, an relative humidity sensor, and an ambient temperature sensor.

51. The system according to claim 50 wherein the system stops air flow if the sensor reports a value beyond a threshold.

52. The system according to claim 50 wherein the system adjusts air flow based on a value generated by the sensor.

53. The system according to claim 50 wherein the system adjusts air temperature based on a value generated by the sensor.

54. The system according to claim 44 further comprising:
a heater for heating air before entry into the reaction chamber.

55. The system according to claim 44 further comprising:
a light source.

56. The system according to claim 55 wherein the light source emits ultraviolet light.

57. The system according to claim 44 further comprising:
an air filter for removing chlorine dioxide from ambient gas.

58. The system according to claim 57 wherein the filter is an activated carbon filter.

59. The system according to claim 44 wherein the reaction chamber further comprises a mixer and the system further comprises a driver.

60. The system according to claim 59 wherein energy is magnetically transferred from the driver to the mixer.

61. The system according to claim 59 wherein the mixer and the driver are mechanically coupled.

62. The system according to claim 44 wherein the reaction chamber further comprises a mixer driven by air flow from the inlet.

63. The system according to claim 44 further comprising:
an external sensor for detecting a concentration of a gas.

64. The system according to claim 63 wherein the external sensor is in communication with the regulator.

65. The system according to claim 44 further comprising:
a detachable display.

66. The system according to claim 65 wherein the system is configured to begin gas generation at a defined interval from the removal of the detachable display from the system.

67. The system according to claim 65 wherein the detachable display indicates an amount of time remaining in a gas generation cycle.

68. The system according to claim 44 further comprising:
a gas dispersal device connected to the outlet.

69. The system according to claim 68 wherein the gas dispersal device is a fan.

70. The system according to claim 68 wherein the gas dispersal device is a mister.

71. A reaction chamber for the generation of a gas comprising:
a first chamber;
a second chamber;
an interface between the first chamber and the second chamber, the interface allowing contents of the first chamber to enter the second chamber at a desired time; and
a neutralizing agent that is mechanically released at a desired time.

72. The reaction chamber according to claim 71 wherein the gas is chlorine dioxide.

73. The reaction chamber according to claim 71 further comprising:
an inlet to the first chamber.

74. The reaction chamber according to claim 73 wherein the inlet comprises a membrane that is mechanically ruptured when the reaction chamber is inserted in a generator.

75. The reaction chamber according to claim 73 wherein the inlet comprises a membrane that is ruptured by a change in pressure.

76. The reaction chamber according to claim 73 wherein the inlet comprises a septum that is punctured when the reaction chamber is inserted in a generator.

77. The reaction chamber according to claim 71 wherein the interface is a check valve.

78. The reaction chamber according to claim 71 wherein the reaction chamber accommodates ice formation within the reaction chamber.

* * * * *